(12) United States Patent
Cowe (10) Patent No.: US 8,425,460 B2
(45) Date of Patent: Apr. 23, 2013

(54) NEEDLE SHROUD ASSEMBLY (75) Inventor: Toby Cowe, Oxford (GB)

(73) Assignee: Owen Mumford Limited, Oxford (GB)

( * ) Notice: Subject to any disclaimer, the term of this patent is extended or adjusted under 35 U.S.C. 154(b) by 0 days.

(21) Appl. No.: 12/065,509

(22) PCT Filed: Sep. 1, 2006

(86) PCT No.: PCT/GB2006/003246
§ 371 (c)(1),
(2), (4) Date: Apr. 7, 2008

(87) PCT Pub. No.: WO2007/026163
PCT Pub. Date: Mar. 8, 2007

(65) Prior Publication Data
US 2008/0215001 A1 Sep. 4, 2008

(30) Foreign Application Priority Data

Sep. 1, 2005 (GB) .................................. 0517699.5
Sep. 1, 2005 (GB) .................................. 0517701.9

(51) Int. Cl.
A61M 5/00 (2006.01)
A61M 5/32 (2006.01)

(52) U.S. Cl.
USPC ............ 604/110; 604/111; 604/263; 604/198

(58) Field of Classification Search ................... 604/110, 604/111, 192, 164.01, 194, 195
See application file for complete search history.

(56) References Cited

U.S. PATENT DOCUMENTS

| 4,664,654 | A | 5/1987 | Strauss |
| 4,863,436 | A | 9/1989 | Glick |
| 4,887,998 | A | 12/1989 | Martin et al. |
| 4,894,055 | A | 1/1990 | Sudnak |
| 4,900,311 | A * | 2/1990 | Stern et al. .................... 604/198 |
| 4,911,693 | A * | 3/1990 | Paris .............................. 604/192 |
| 4,917,673 | A | 4/1990 | Coplin |
| 4,946,446 | A | 8/1990 | Vadher |
| 4,985,021 | A | 1/1991 | Straw et al. |
| 4,994,045 | A | 2/1991 | Ranford |

(Continued)

FOREIGN PATENT DOCUMENTS

| EP | 0 506 204 | 9/1992 |
| EP | 0 575 492 | 12/1993 |

(Continued)

OTHER PUBLICATIONS

Japanese Office Action, dated Jul. 12, 2011, in Application No. 2008-528578.

Primary Examiner — Nicholas Lucchesi
Assistant Examiner — Jenna Zhang
(74) Attorney, Agent, or Firm — Young & Thompson (57) ABSTRACT A needle shroud assembly for a syringe holder comprises a barrel (16), a needle shroud (24) captively telescoped relative to the forward end of the barrel (16) and retained by a top outer body (44). A locking ring (42) cooperates with the shroud, having diametrically opposed keyways which are brought into and out of axial alignment with keys (38) on the shroud (24) to free or lock the shroud from movement. The locking collar (42) is biased towards a 'safe' position. On cocking the locking ring (42) to a 'live' position the shroud (24) is freed for retraction movement but on return to its extended position, the locking ring is returned to its 'safe' position.

10 Claims, 6 Drawing Sheets

U.S. PATENT DOCUMENTS

| | | |
|---|---|---|
| 4,998,924 A | 3/1991 | Ranford |
| 5,013,302 A | 5/1991 | Schmidt |
| 5,019,051 A | 5/1991 | Hake |
| 5,024,660 A | 6/1991 | McNaughton |
| 5,049,136 A | 9/1991 | Johnson |
| 5,053,018 A | 10/1991 | Talonn et al. |
| 5,057,079 A | 10/1991 | Tiemann et al. |
| 5,057,086 A | 10/1991 | Dillard, III et al. |
| 5,057,087 A | 10/1991 | Harmon |
| 5,088,986 A | 2/1992 | Nusbaum |
| 5,088,988 A | 2/1992 | Talonn et al. |
| 5,104,384 A | 4/1992 | Parry |
| 5,106,379 A | 4/1992 | Leap |
| 5,127,910 A | 7/1992 | Talonn et al. |
| 5,141,500 A | 8/1992 | Hake |
| 5,147,326 A | 9/1992 | Talonn et al. |
| 5,147,327 A | 9/1992 | Johnson |
| 5,160,326 A | 11/1992 | Talonn et al. |
| 5,169,392 A | 12/1992 | Ranford et al. |
| 5,181,524 A | 1/1993 | Wanderer et al. |
| 5,201,720 A | 4/1993 | Borgia et al. |
| 5,201,721 A | 4/1993 | Lee et al. |
| 5,217,437 A | 6/1993 | Talonn et al. |
| 5,232,457 A | 8/1993 | Grim |
| 5,242,416 A | 9/1993 | Hutson |
| 5,246,428 A | 9/1993 | Falknor |
| 5,252,401 A | 10/1993 | Kitto et al. |
| 5,256,153 A | 10/1993 | Hake |
| 5,267,976 A | 12/1993 | Guerineau et al. |
| 5,269,761 A | 12/1993 | Stehrenberger et al. |
| 5,269,766 A | 12/1993 | Haber et al. |
| 5,279,584 A | 1/1994 | Dillard, III et al. |
| 5,295,965 A | 3/1994 | Wilmot |
| 5,312,370 A | 5/1994 | Talonn et al. |
| 5,314,414 A | 5/1994 | Hake et al. |
| 5,364,360 A | 11/1994 | Flumene et al. |
| 5,376,080 A | 12/1994 | Petrussa |
| 5,389,085 A | 2/1995 | D'Alessio et al. |
| 5,403,287 A | 4/1995 | Talonn et al. |
| 5,415,645 A | 5/1995 | Friend et al. |
| 5,433,712 A | 7/1995 | Stiles et al. |
| 5,472,430 A | 12/1995 | Vaillancourt et al. |
| 5,522,812 A | 6/1996 | Talonn et al. |
| 5,549,558 A | 8/1996 | Martino |
| 5,554,122 A | 9/1996 | Emanuel |
| 5,554,130 A | 9/1996 | McDonald et al. |
| 5,573,513 A | 11/1996 | Wozencroft |
| 5,609,577 A | 3/1997 | Haber et al. |
| 5,658,254 A | 8/1997 | Reichenbach et al. |
| 5,674,203 A | 10/1997 | Lewandowski |
| 5,688,241 A | 11/1997 | Asbaghi |
| 5,709,662 A | 1/1998 | Olive et al. |
| 5,733,264 A | 3/1998 | Flowers |
| 5,743,887 A | 4/1998 | Brattesani |
| 5,795,336 A | 8/1998 | Romano et al. |
| 5,843,036 A | 12/1998 | Olive et al. |
| 5,843,041 A | 12/1998 | Hake et al. |
| 5,843,047 A | 12/1998 | Pyrozyk et al. |
| 5,976,111 A | 11/1999 | Hart |
| 5,980,494 A | 11/1999 | Malenchek et al. |
| 5,984,899 A | 11/1999 | D'Alessio et al. |
| 6,013,059 A | 1/2000 | Jacobs |
| 6,017,329 A | 1/2000 | Hake |
| 6,030,366 A | 2/2000 | Mitchell |
| 6,099,503 A | 8/2000 | Stradella |
| 6,186,980 B1 | 2/2001 | Brunel |
| 6,210,369 B1 | 4/2001 | Wilmot et al. |
| 6,270,479 B1 | 8/2001 | Bergens et al. |
| 6,371,939 B2 | 4/2002 | Bergens et al. |
| 6,416,323 B1 | 7/2002 | Grenfell et al. |
| 6,419,658 B1 | 7/2002 | Restelli et al. |
| 6,544,234 B1 | 4/2003 | Gabriel |
| 6,569,124 B1 | 5/2003 | Perouse |
| 6,575,939 B1 | 6/2003 | Brunel |
| 6,648,858 B2 | 11/2003 | Asbaghi |
| 6,852,096 B1 | 2/2005 | Pouget et al. |
| 6,960,194 B2 | 11/2005 | Hommann et al. |
| 7,004,930 B2 | 2/2006 | Marshall |
| 2002/0004652 A1 | 1/2002 | Asbaghi |
| 2002/0165500 A1 | 11/2002 | Bechtold et al. |
| 2003/0120209 A1 | 6/2003 | Jensen et al. |
| 2004/0122379 A1* | 6/2004 | Bosse et al. .................. 604/263 |
| 2004/0225262 A1* | 11/2004 | Fathallah et al. ............ 604/198 |
| 2005/0049561 A1 | 3/2005 | Hommann et al. |
| 2005/0065476 A1 | 3/2005 | Jensen et al. |
| 2005/0228345 A1 | 10/2005 | Yang et al. |

FOREIGN PATENT DOCUMENTS

| | | |
|---|---|---|
| EP | 1 039 942 | 10/2000 |
| EP | 1 124 601 | 8/2001 |
| EP | 1 285 674 | 2/2003 |
| EP | 1 452 197 | 9/2004 |
| GB | 2 414 400 | 11/2005 |
| JP | 2004502501 A | 1/2004 |
| WO | 92/18183 | 10/1992 |
| WO | 93/11816 | 6/1993 |
| WO | 93/13819 | 7/1993 |
| WO | 98/10816 | 3/1998 |
| WO | 98/10816 A | 3/1998 |
| WO | 00/16830 | 3/2000 |
| WO | 01/68164 A1 | 9/2001 |
| WO | 01/76665 | 10/2001 |
| WO | 0204053 A1 | 1/2002 |
| WO | 03/045481 | 6/2003 |
| WO | 2005/030301 | 4/2005 |
| WO | 2005/035029 | 4/2005 |
| WO | 2005/035030 | 4/2005 |

* cited by examiner

NEEDLE SHROUD ASSEMBLY

This invention relates to a needle shroud assembly and to injection devices incorporating such assemblies.

A medical syringe is often placed in a pen-like firing device or a holder of barrel form. The more sophisticated devices have a trigger which, when actuated, causes the dose to be administered automatically. The barrel-like holders make handling the syringe easier, but however the syringe is mounted, its needle has to project from the forward end, at least at the time of administering the dose. At other times, it is highly desirable for the syringe needle to be shrouded to prevent needle-stick injuries. It is also desirable to hide the needle in cases of patient needle phobia.

It is known to provide needle shroud assemblies in which an integral sprung latch is mounted on either the barrel or the shroud and is unlatched by pressing an externally accessible button so freeing the shroud for retraction movement. The use of an integral latch has problems associated with it because the design of the latch is inevitably a compromise between the requirement for the appropriate degree of flexural stiffness, the required robustness of the latch and the extent of the mutual abutment surfaces when the two items are latched together.

Accordingly, in one aspect, this invention provides a needle shroud assembly for a syringe holder, said assembly comprising:

a barrel;

a needle shroud captively telescoped relative to the forward end of the barrel for movement between an extended position and a retracted position;

shroud bias means urging said shroud towards said extended position, and a locking element mounted for movement between a safe position in which retraction movement of said needle shroud is prevented or limited, and a live position in which said needle shroud may pass towards its retracted position;

one of said shroud and said locking element having a keyway and the other thereof having a cooperating key arranged such that relative movement of said key with respect to said keyway is obstructed when said locking element is in its safe position.

The term 'key' is used broadly to mean a projecting element that cooperates with a keyway. The term 'keyway' is used broadly to mean a structural or non-structural path along which a key may pass. It may be a groove, or slot, or it may be an unobstructed region bordered along the path or at one end thereof by an abutment surface, to just one or both sides of the path. It should be noted that the reference to obstruction of movement does not preclude initial movement prior to encounter with said obstruction.

Preferably said needle shroud is provided with said key and said locking element is provided with said keyway, although the opposite arrangement is possible.

Preferably said locking element comprises a locking collar mounted for limited rotational movement relative to said barrel and having an externally accessible actuating portion. The locking element is preferably biased by bias means towards its safe position. The bias means may be a separate spring or it may be integrally formed with said locking element or a component in proximity thereto.

Preferably a latch arrangement is provided to retain the locking element in its live position on initial movement thereto from said safe position. The latching action gives a positive confirmation that the device is unlocked or 'live'. The latch arrangement may comprise a latch on one of said locking element and said needle shroud (or a part associated therewith), and at least one latch recess on the other thereof. The latch may typically be provided on the locking element with the latch recess provided on the needle shroud.

The latch may be of saw tooth form with the latch recess being correspondingly shaped, to provide a click action on latching.

In a particularly preferred embodiment, on moving said locking element to its live position, initial retraction movement of the needle shroud effects release of said latch so that said locking element may return to its safe position once the needle shroud has returned to or near its fully extended position.

Whilst the invention has been described above, it extends to any inventive feature set out above or in the following description.

The invention may be performed in various ways and an embodiment thereof will now be described by way of example only, reference being made to the accompanying drawings, in which:

FIGS. 4(*a*), (*b*) and (*c*) are respective side, cross-section and top views of the first embodiment of needle shroud assembly in accordance with this invention;

FIGS. 5(*a*) and (*b*) to FIGS. 12(*a*) and (*b*) are respective section and top views of first embodiment of the needle shroud assembly of FIGS. 4(*a*) to (*c*) in successive stages through a cycle of operation;

Figure 1:
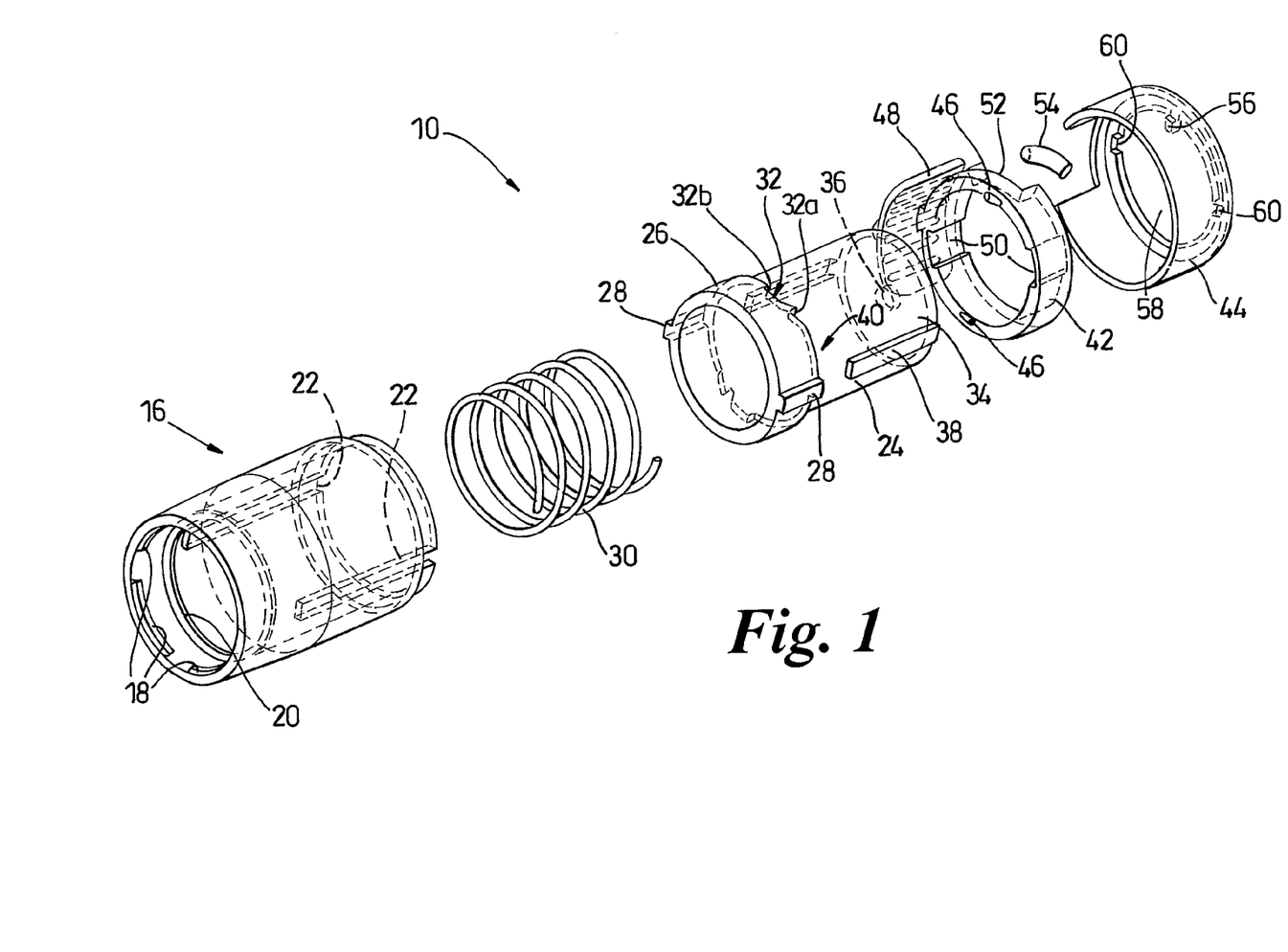
FIG. 1 is an exploded view of a first embodiment of needle shroud assembly in accordance with this invention.
Figures 2, 3:
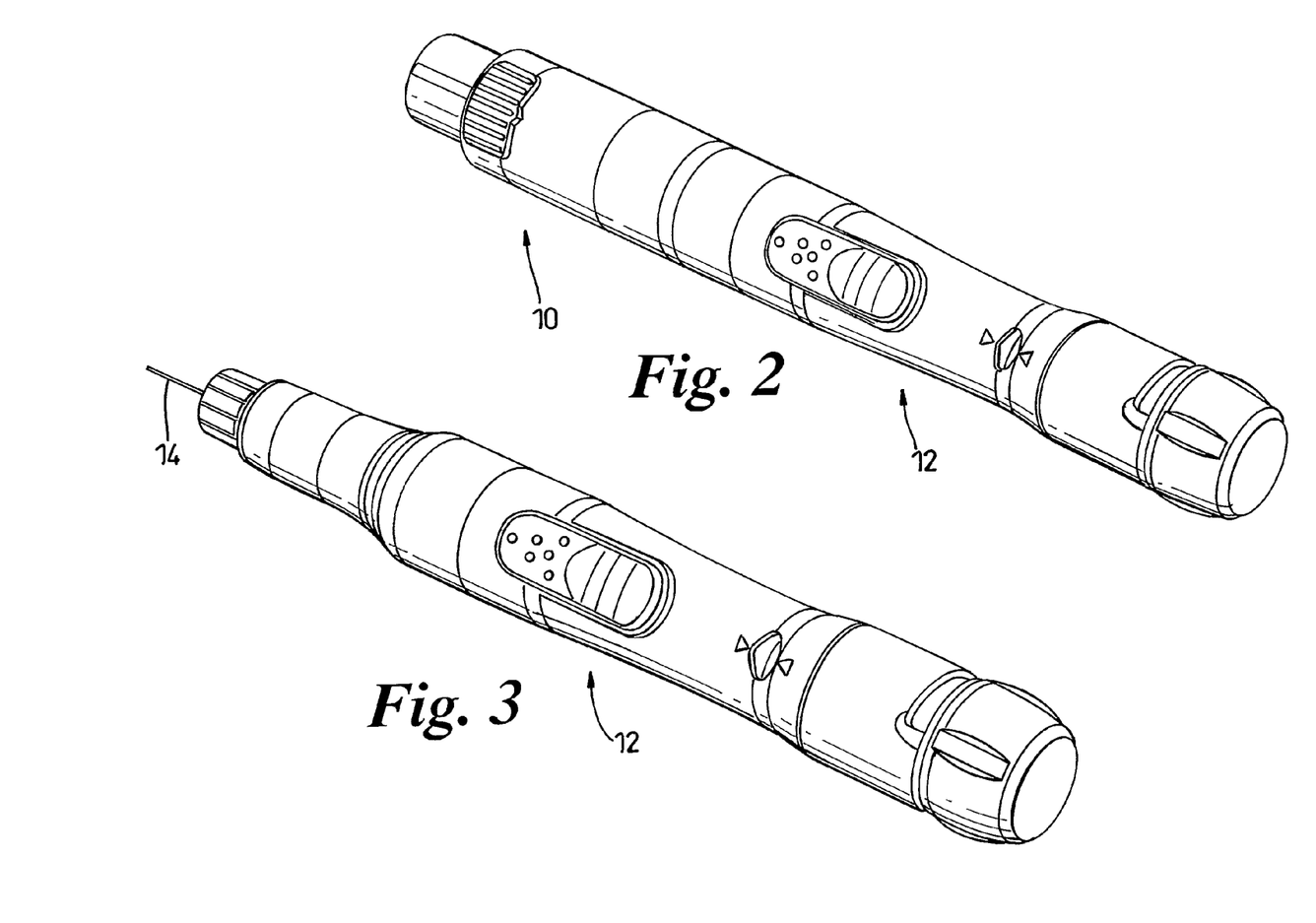
FIG. 2 is a view of an injection device fitted with the first embodiment of a needle shroud assembly in accordance with this invention.
FIG. 3 is a view similar to FIG. 2 but with the needle shroud assembly removed.

Referring initially to FIGS. 1 to 3, the first embodiment of needle shroud assembly 10 of this invention is intended to be fitted to an injection device 12 designed to hold a syringe (not shown) and to meter out a measured dose via a needle 14. The needle shroud assembly 10 is designed to lock a retractable needle shroud 16 in an extended position as shown in FIG. 2 in which it shrouds a needle to prevent possible injury, until such time as the user wishes to inject themselves.

Referring now particularly to FIG. 1, the needle shroud assembly 10 comprises a barrel 16 of plastics material having internal rib formations 18 at its rearward end to allow it to be removably attached to the injection device by screw thread or click action. Forward of the formations 18 is an annular rib 20 and forward of that two diametrically opposed guide grooves 22. Telescopically received in the barrel 16 is a needle shroud 24 having a collar 26 at its rear end with diametrically opposed ribs 28 which run in the guide grooves 22, with the needle shroud 24 being urged forwardly by means of a compression spring 30, acting between an internal seat (not shown) in the barrel 16, and the collar 26. On its forward facing shoulder the collar 26 has two diametrically opposed latch regions 32 comprising a triangular-shaped recess 32(*a*) and a trapezoidal recess 32(*b*) for cooperation with the locking collar as to be described below. Forward of the collar 26, the needle shroud is generally of hollow cylindrical form having an end wall 34 with a central needle hole 36. Down each external side of the cylindrical wall, angularly aligned with but set radially inwardly of the ribs 28 are two longitudinal key formations 38. The key formations are spaced from the forward facing shoulder of the collar 26 by a gap 40.

Fitting over the forward end of the needle shroud 24 is a locking sleeve 42, with a top outer body 44 passing over the locking sleeve 42 to connect to the forward end of the barrel 16. The arrangement is such that the locking sleeve 42 is clamped between the top outer body 44 and the collar 26 on the needle shroud 24 by action of the compression spring 30.

The locking sleeve 42 has on its rearward facing surface two diametrically opposed triangular teeth 46 which cooperate with the respective latch regions 32 on the collar 26 as to be described below. The locking sleeve 42 has an externally accessible thumb plate 48 and two diametrically opposed keyways 50 designed to be somewhat wider than the key formations 38. On its forward surface, the locking sleeve 42 is cut away as shown at 52 to provide an abutment surface which engages one end of a compression spring 54, the other end of which engages a corresponding abutment surface 56 in the top outer body 44 to urge the docking sleeve counter-clockwise as viewed in FIG. 1. Although shown as a separate spring 54, this spring could be formed integrally with e.g. the locking sleeve 42. The top outer body 44 has an end aperture 58 through which the needle shroud 24 may slide, with diametrically opposed notches 60 through which run the key formations 38.

Turning to the latch arrangement, the axial extent of the locking sleeve 42 adjacent the keyways 50 is the same as that of the gap 40 between the key formations 38 and the forward shoulder of the collar 26 (or slightly larger) so that the locking sleeve can be rotated between a position in which the keyways 50 can receive the key formations 38, so that the locking sleeve does not restrain longitudinal movement of the sleeve 24, to a position in which the keyways 50 are offset from the key formations 38, thereby blocking retraction movement. These positions referred to as the 'live' and 'safe' positions respectively.

When in the safe position, the teeth 46 on the locking sleeve 42 are disposed in the trapezoidal portions 32(b) of the latch region 32 and the compression spring 54 urges the teeth 46 so that, for each, the axial face is in engagement with the axial face of the trapezoidal section 32(b). When the user moves the locking sleeve 42 to its live position using the thumb plate 48, the teeth 46 move clockwise as seen in FIG. 1 so that their inclined surfaces contact and ride over the corresponding inclined surfaces of the saw tooth formations defined between the trapezoidal and triangular sections 32(b) and 32(a). There is a corresponding slight retraction movement of the needle shroud sleeve 24 reacted by the compression spring 30, as the teeth 46 move over the hump and then drop back into the triangular recesses 32(a) when the locking sleeve has reached the live position. The size of the gap 40 is just enough to accommodate this, but small enough to ensure that the shield is prevented from travelling back when the device is locked.

The user then places the needle shroud end wall 34 against their skin and applies pressure so that the needle shroud 24 starts to retract against the force of the compression spring 30. However, retraction of the needle shroud 24 moves the latch region 32 away from the locking teeth 46 and as soon as the teeth 46 are clear of the triangular regions 32(a) the locking sleeve 42 is free to rotate counter-clockwise under the influence of the compression spring 54. It is not free to return fully to the safe position because by this time the key formations 38 are running in the keyways 50 with the counter-clockwise trailing surface of the grooves 50 in sliding contact with the corresponding surfaces of the key formations 38.

On completion of the injection and taking the shroud assembly out of contact with the skin, the needle shroud extends under the influence of the spring 30 until the gap 40 on the needle shroud 24 is in registration with the locking sleeve 42 so that it can return fully to its safe position.

Figure 4:
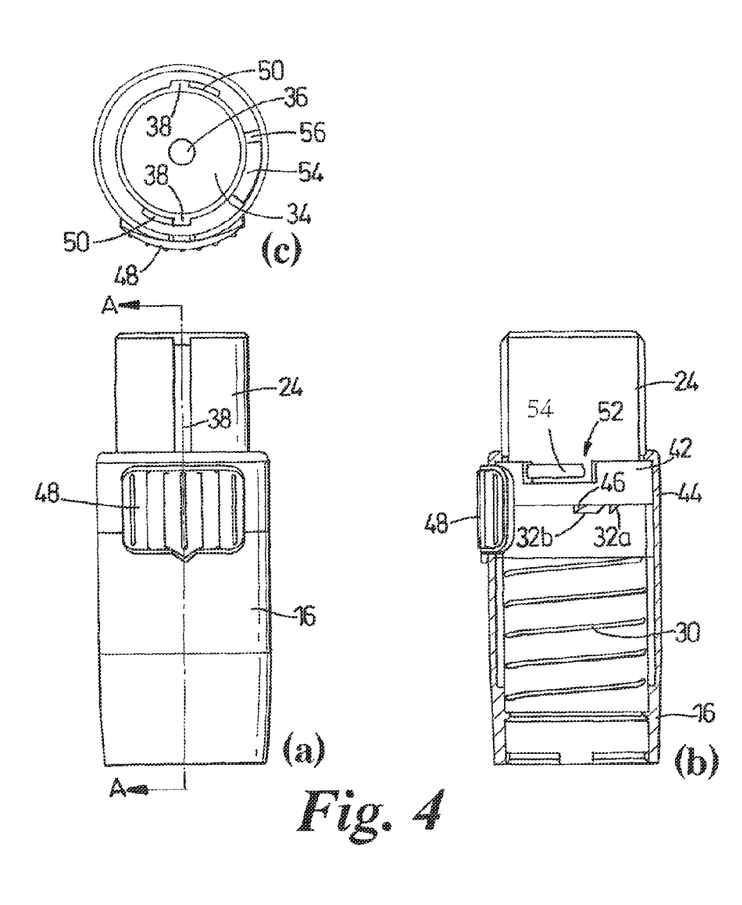
Figure 5:
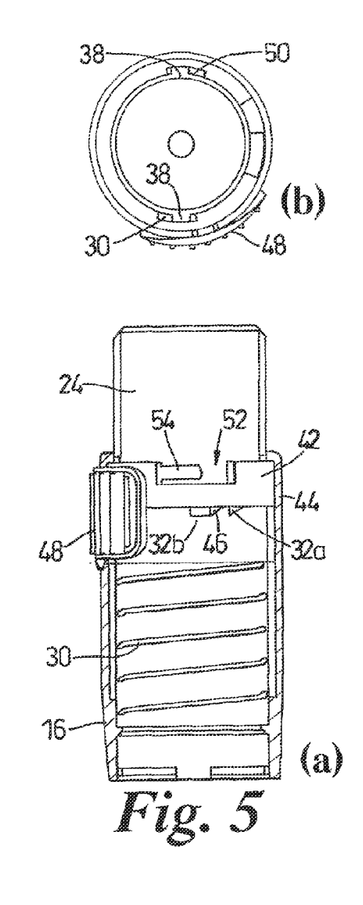
Figure 6:
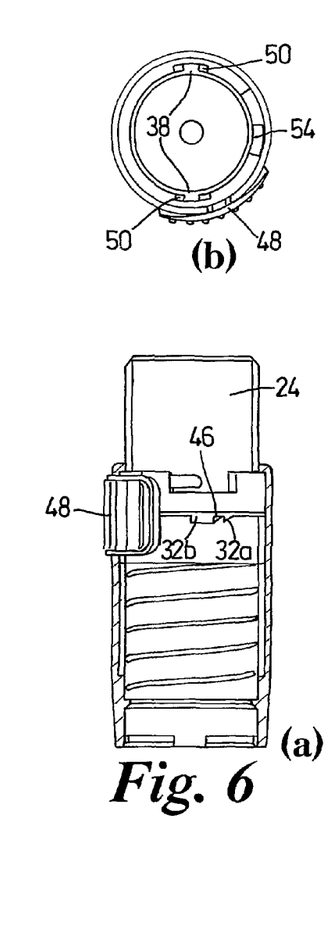
Figure 7:
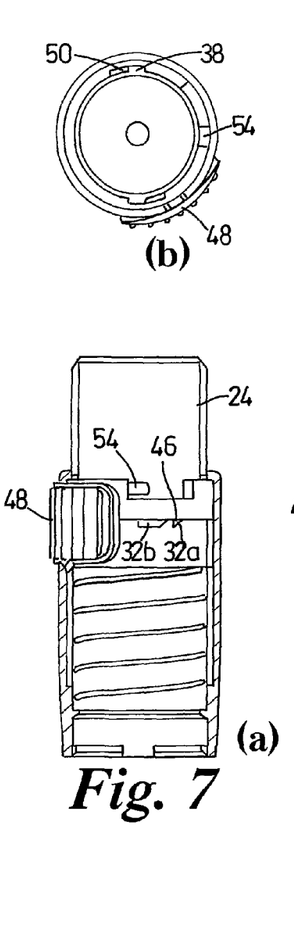

Turning now to FIGS. 4(a) to (c) to FIG. 12(a) and (b), in the safe position shown in FIGS. 4(a) to (c), the thumb plate 48 is in the safe position, the tooth 46 on the locking ring 42 is positioned to the left hand end of the trapezoidal locking section 32(b) and the spring 54 is at its fullest length. From this position the user rotates the thumb plate 48 counter-clockwise (as viewed in top view) so that the tooth 46 moves to the right hand end of the trapezoidal recess 32(b) (FIG. 5(a)), the spring 54 is partially compressed and the key formations 38 align with one end of the keyways 50 as can be seen in the top view (FIG. 5(b)). On further rotation of the thumb plate the tooth 46 rides up the corresponding tooth shape between the recesses 32(b) and 32(a) causing slight retraction movement of the needle shroud (FIG. 6(a)) and the key formations 38 are generally central in the keyways 50 (FIG. 6(b)). Beyond this the tooth 46 drops into the recess 32(a) (FIG. 7(a)) with the key formations 38 then being aligned with the clockwise most end of the keyway 50 (FIG. 7(b)).

Figure 8:
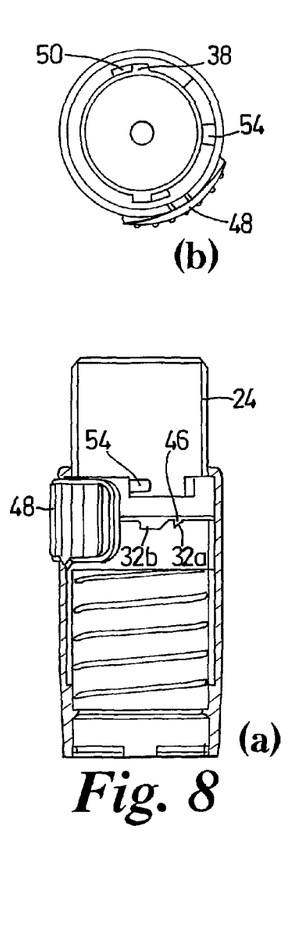
Figure 9:
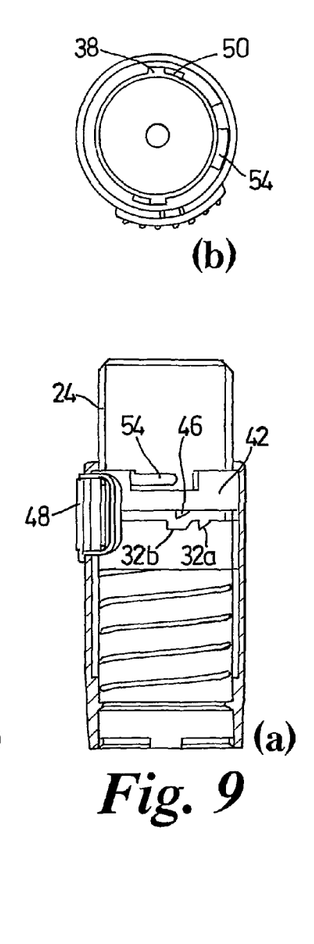
Figure 10:
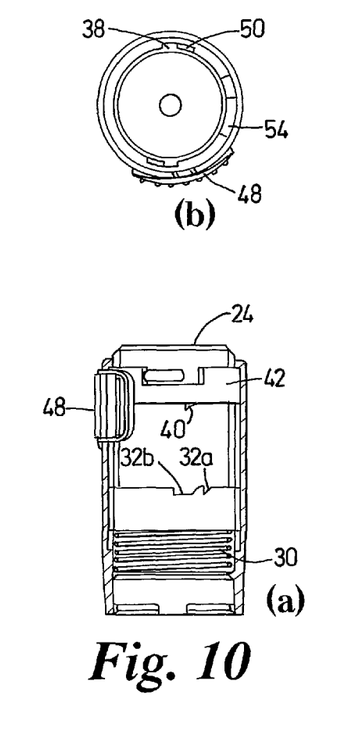
Figure 11:
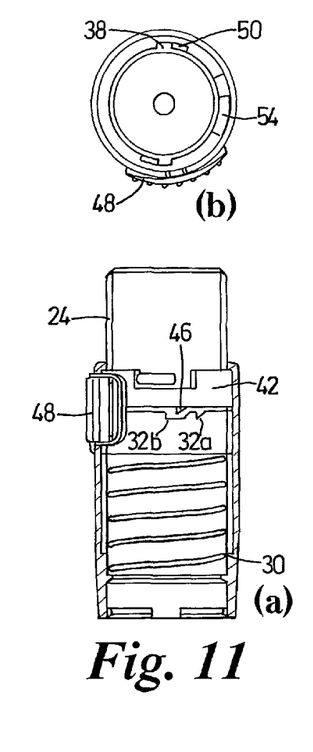
Figure 12:
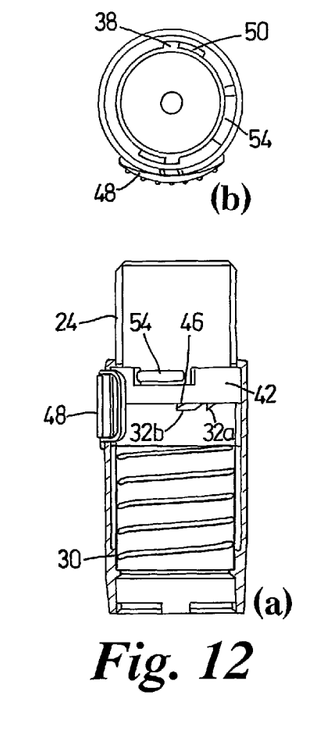

In this position the user will have felt a 'click' indicating that the device is ready to use. On applying the needle shroud 24 to the skin and applying pressure, the needle shroud starts to retract (FIG. 8(a)) and the key formations enter the aligned keyways 50. On further retraction movement, the tooth 46 escapes the triangular recess 32(a) thus freeing the locking sleeve 42 for rotation in the clockwise sense (as viewed in FIG. 9(b)). Rotation of the sleeve 42 is limited by engagement of the facing surfaces on the key formation 38 and the keyway 50. The shroud can be pushed to its fully retracted position against the influence of the spring 30 (FIG. 10(a)). On completion of the injection the needle shroud assembly is withdrawn from the patient's skin so that it returns towards its extended position but the locking sleeve 42 is held away from its safe position by continued engagement of the facing surfaces of the key formation 38 and the keyway 50, so that the tooth 46 is positioned in the middle of the trapezoidal recess 32(b) (FIG. 11(a)). Finally, as the keyway 50 is aligned with the gap 40 on the needle shroud, the locking sleeve is returned to its safe position by the action of the spring 54 (FIG. 12(a)).

It will of course be appreciated that although in this embodiment the (male) keys are on the shroud 26 and the (female) keyways are on the locking collar 42, this arrangement can be reversed with for example an L-shaped keyway on the shroud cooperating with a key on the locking collar.

Figures 13, 14:
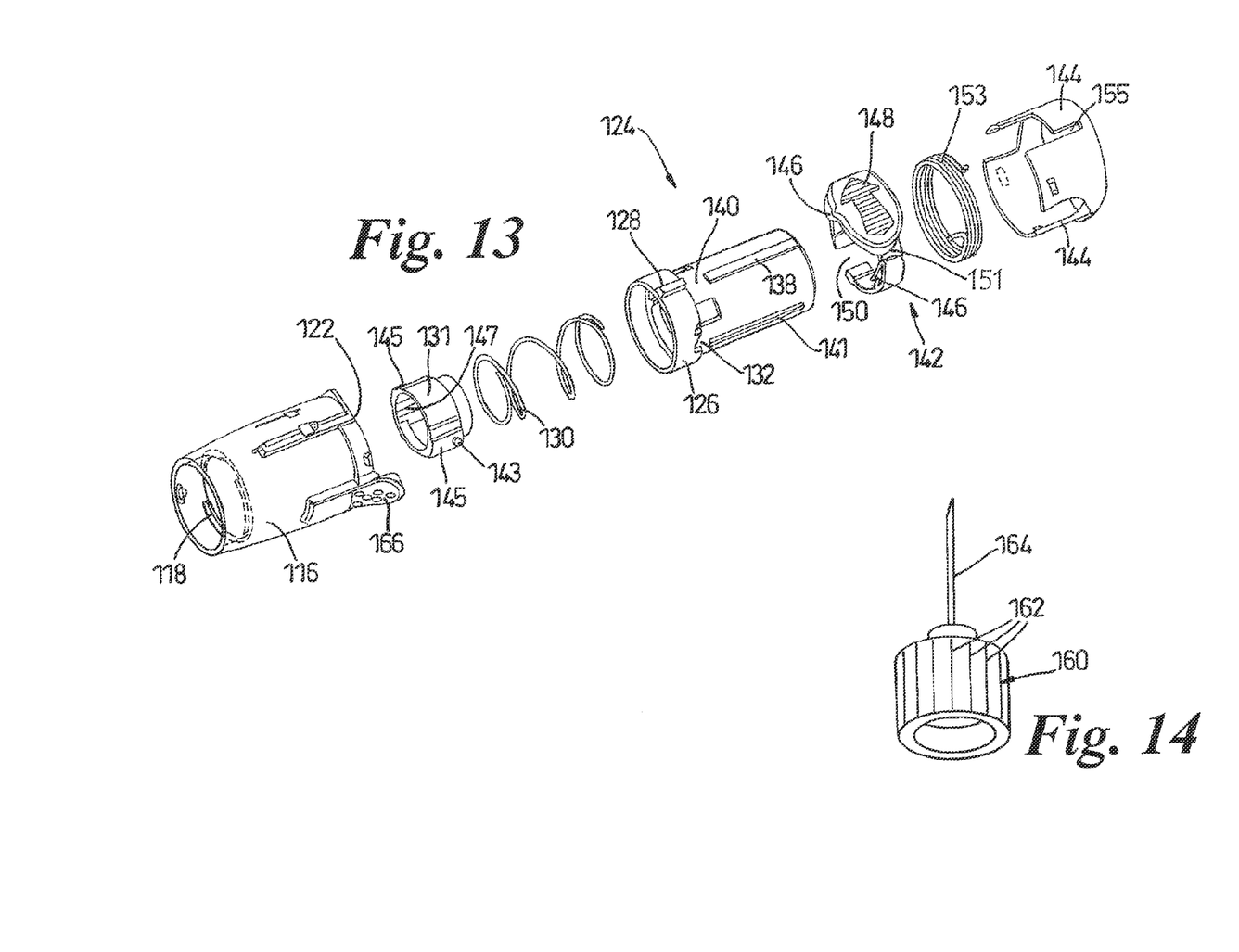
FIG. 13 is an exploded view of a second embodiment of needle shroud assembly in accordance with this invention.
FIG. 14 is a view of a typical needle tip.

FIG. 13 is an exploded view of a second embodiment of a needle shroud assembly of this invention, which is similar in many respects to the first embodiment and so similar components are given similar reference numbers but prefixed by 1. The assembly comprises a barrel 116 having internal rib formations 118, and two opposed guide grooves 122. Telescopically received in the barrel 116 is a needle shroud 124 having a collar 126 at its rear end with diametrically opposed ribs 128 which run in the guide grooves 122. In this embodiment the compression spring 130 acts off the front end of a needle grip ring 131 which in use locates on a needle tip 14 (see FIG. 3) fitted to the end of a cartridge (not shown) held within an injection device of the type as shown in FIGS. 2 and 3. The other end of the spring 130 acts on the collar 126. The collar 126 has two diametrically opposed latch regions 132 only one of which is visible in FIG. 13, and topward of the collar there are longitudinal key formations 138 spaced from the forward facing edge of the collar by a gap 140. At 900 to the formations 138 are slots 141 which receive location pips 143 on opposed formations 145 on the grip ring 131. A locking sleeve 142 fits over the forward end of the needle shroud 124, and is retained by a top outer body 144. The locking sleeve has two diametrically opposed triangular teeth 146 which cooperate with the latch regions 132 as in the previous embodiment, although in this embodiment the release movement of the locking ring is counter-clockwise. The locking ring has an externally accessible thumb plate 148 and two diametrically opposed keyways 150, only one of which is visible in FIG. 13. The visible keyway is a gap defined between the ends of the locking ring, whereas the other keyway is an internally facing groove similar to one of the grooves 50 in the first embodiment. The gap and the groove both function as keyways. The locking sleeve has an externally facing groove 151 which receives one end of a torsion spring 153, the other end of which is located in a slot 155 in the top outer body 144. The torsion spring biases the locking ring clockwise to fulfil a similar function to the compression spring 54 in the first embodiment.

The operation of the locking mechanism is essentially the same as that for the first embodiment and will not be described again.

The grip ring 131 is designed to fit over a needle tip of the type shown in more detail in FIG. 14, comprising an internally threaded collar 160 having external splines 162 and a needle 164. The grip ring has internal splines 147 which cooperate with those of the needle tip to allow rotation to be transmitted from the grip ring 131 to the needle tip. There are two possible arrangements; in one arrangement the grip ring is designed to fit over said needle tip rotationally engaged but with clearance and to be resiliently compressible to grip said collar. In a second arrangement the grip ring is designed to be of elliptical or flattened circular cross-section, with the minor axis being an interference fit on said needle tip and the major axis being resiliently compressible to release said interference fit.

The barrel 116 is provided with two diametrically opposed resiliently flexible tongues 166 which align with the pips 143 and/or the formations 145. On completion of an injection, the barrel 116 may be rotated relative to the remainder of the injection device 12, to rotate the grip ring 131 and thus the needle tip, to unscrew it from the cartridge. Having undone the needle tip it then needs to be pulled clear of the septum in the cartridge, so that the contained needle tip, can be safely disposed of. In the first mentioned arrangement the flexible tongues 166 are squeezed by the user so the needle tip is firmly gripped, and the assembly then removed, held over a sharps bin and pressure released on the tongues 166 to allow the needle tip to drop into the bin. In the second arrangement, the tongues are squeezed only after removal of the assembly, to release the needle tip.

Attention is directed to our co-pending U.S. patent application Ser. No. 12/065,512 with a PCT filing date of Sep. 1, 2006, (PCT Application PCT/GB2006/003248) the entire contents of which are incorporated by reference, and a copy of which accompanied the application papers.

The invention claimed is:

1. A needle shroud assembly for an injection device, said assembly comprising:
a barrel;
a needle shroud captively telescoped relative to the forward end of the barrel for longitudinal movement between an extended position and a retracted position;
a shroud bias urging said needle shroud towards said extended position; and
a locking collar mounted for rotational movement with respect to said barrel and with respect to said needle shroud between a safe position in which retraction movement of said needle shroud is prevented or limited, and a live position in which said needle shroud may pass towards the retracted position, said locking collar being manually and externally actuatable,
wherein one of said needle shroud and said locking collar has a keyway and the other thereof has a cooperating key arranged so that said key and said keyway being out of alignment obstructs relative longitudinal movement of said key with respect to said keyway when said locking collar is in the safe position and so that said key and said keyway being aligned does not obstruct relative longitudinal movement of said key with respect to said keyway when said locking collar is in the live position.

2. The needle shroud assembly according to claim 1, wherein said needle shroud is provided with said key and said locking collar is provided with said keyway.

3. The needle shroud assembly according to claim 1, wherein the locking collar is biased by a collar bias towards the safe position.

4. The needle shroud assembly according to claim 3, wherein the collar bias is a separate spring.

5. The needle shroud assembly according to claim 3, wherein the collar bias is integrally formed with said locking collar or a component in proximity thereto.

6. The needle shroud assembly according to claim 1, wherein a latch arrangement is provided to retain the locking collar in the live position on initial movement thereto from said safe position.

7. The needle shroud assembly according to claim 6, wherein the latch arrangement comprises a latch on one of said locking collar and said needle shroud, and at least one latch recess on the other thereof.

8. The needle shroud assembly according to claim 7, wherein the latch is of saw tooth form with the latch recess being correspondingly shaped.

9. The needle shroud assembly according to claim 6, wherein, having moved said locking collar to the live position, initial retraction movement of the needle shroud effects release of said retained latch so that said locking collar may return to the safe position once the needle shroud has returned to or near the extended position to prevent retraction of said needle shroud.

10. A needle shroud assembly for an injection device, said assembly comprising:
a barrel;
a needle shroud captively telescoped relative to the forward end of the barrel for longitudinal movement between an extended position and a retracted position;
a shroud bias urging said needle shroud towards said extended position; and
a locking element movably mounted, with respect to both said needle shroud and said barrel, for movement in a plane generally transverse to said longitudinal direction between a safe position in which retraction movement of said needle shroud is prevented, and a live position in which said needle shroud may pass towards the retracted position;
wherein said locking element and said needle shroud have respective abutment surfaces that are arranged so that said respective abutment surfaces being out of alignment obstructs relative longitudinal movement of said respective abutment surfaces when said locking element is in the safe position and so that said respective abutment surfaces being aligned does not obstruct relative longitudinal movement of said respective abutment surfaces when said locking collar is in the live position.

* * * * *

UNITED STATES PATENT AND TRADEMARK OFFICE
CERTIFICATE OF CORRECTION

PATENT NO. : 8,425,460 B2  
APPLICATION NO. : 12/065509  
DATED : April 23, 2013  
INVENTOR(S) : Toby Cowe Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 61 days.

Signed and Sealed this
Eighth Day of September, 2015

Michelle K. Lee
*Director of the United States Patent and Trademark Office*